(12) United States Patent
Shelley et al.

(10) Patent No.: US 8,519,337 B2
(45) Date of Patent: *Aug. 27, 2013

(54) THERMAL EFFECT MEASUREMENT WITH NEAR-INFRARED SPECTROSCOPY

(75) Inventors: Paul Shelley, Lakewood, WA (US);
Greg Werner, Puyallup, WA (US); Paul Vahey, Seattle, WA (US)

(73) Assignee: The Boeing Company, Chicago, IL (US)

( * ) Notice: Subject to any disclaimer, the term of this patent is extended or adjusted under 35 U.S.C. 154(b) by 838 days.

This patent is subject to a terminal disclaimer.

(21) Appl. No.: 12/164,017

(22) Filed: Jun. 28, 2008

(65) Prior Publication Data
US 2011/0108731 A1    May 12, 2011

(51) Int. Cl.
*G01N 21/3581* (2006.01)
*G01N 21/35* (2006.01)

(52) U.S. Cl.
USPC ..................... 250/341.8; 250/341.6

(58) Field of Classification Search
USPC ................. 250/252.1, 341.6, 341.8; 374/45
See application file for complete search history.

(56) References Cited

U.S. PATENT DOCUMENTS

| | | | |
|---|---|---|---|
| 4,483,629 A | 11/1984 | Schwarz et al. | |
| 5,209,569 A | 5/1993 | Fujiwara et al. | |
| 5,638,284 A | 6/1997 | Helmer et al. | |
| 5,945,676 A | 8/1999 | Khalil et al. | |
| 5,965,888 A | 10/1999 | Engstrom et al. | |
| 6,434,267 B1 | 8/2002 | Smith | |
| 6,495,833 B1 | 12/2002 | Alfano et al. | |
| 6,623,159 B2 | 9/2003 | Takahara et al. | |
| 6,784,431 B2 | 8/2004 | Shelley et al. | |
| 6,794,651 B2 | 9/2004 | Shelley et al. | |
| 6,903,339 B2 | 6/2005 | Shelley et al. | |
| 6,906,327 B2 | 6/2005 | Shelley et al. | |
| 7,064,331 B2 | 6/2006 | Rothenfusser et al. | |
| 7,115,869 B2 | 10/2006 | Shelley et al. | |
| 7,223,977 B2 | 5/2007 | Shelley et al. | |
| 7,897,923 B2 * | 3/2011 | Shelley et al. | ........... 250/339.11 |
| 2002/0107644 A1 | 8/2002 | Meglen et al. | |
| 2002/0109093 A1 | 8/2002 | Kelley | |
| 2002/0113212 A1 * | 8/2002 | Meglen et al. | ........... 250/339.05 |
| 2002/0167988 A1 | 11/2002 | Zhu | |
| 2004/0155190 A1 | 8/2004 | Shelley et al. | |

(Continued)

FOREIGN PATENT DOCUMENTS

| | | | |
|---|---|---|---|
| EP | 2138829 A1 | 12/2009 | |
| EP | 2138830 A2 | 12/2009 | |
| WO | WO 2008048705 A2 * | 4/2008 | |

OTHER PUBLICATIONS

Janke et al (1993). "Composite Heat Damage Assessment." OSTI ID: 245551, p. 1-16.*

(Continued)

*Primary Examiner* — David Porta
*Assistant Examiner* — Casey Bryant
(74) *Attorney, Agent, or Firm* — Parsons Behle & Latimer

(57) ABSTRACT

A method of determining a physical property of a composite material includes providing a series of composite materials surfacing films, which are subjected to increasing thermal experience to create a set of thermal effect standards, collecting near-IR spectra on those standards, performing data pre-processing and then multivariate calibration on the spectra of the composite materials surfacing films, and using that calibration to predict the thermal effect for samples in question.

17 Claims, 5 Drawing Sheets

(56) References Cited

U.S. PATENT DOCUMENTS

| | | | |
|---|---|---|---|
| 2004/0159789 | A1 | 8/2004 | Treado et al. |
| 2005/0067569 | A1 | 3/2005 | Shelley et al. |
| 2007/0009009 | A1 | 1/2007 | Dziki |
| 2007/0131862 | A1 | 6/2007 | Cowan et al. |
| 2009/0321647 | A1* | 12/2009 | Shelley et al. ............ 250/339.07 |
| 2009/0321648 | A1* | 12/2009 | Shelley et al. ............ 250/339.11 |
| 2009/0323757 | A1* | 12/2009 | Werner et al. .................... 374/45 |
| 2010/0038544 | A1* | 2/2010 | Shelley et al. ............ 250/339.09 |
| 2011/0001047 | A1* | 1/2011 | Shelley et al. ............. 250/341.8 |

OTHER PUBLICATIONS

Fisher et al. (1995). "Non Destructive Inspection of Graphite-Epoxy Compsites for Heat Damage Using Laser-Induced Fluorescence." Applied Spectroscopy 46 (9):1225-1231.*

Hamid, S.H. (2000), Ultraviolet-induced degradation of Ziegler-Natta and metallocene catalyzed polyethylenes; Journal of Applied Polymer Science, 78: 1591-1596.

Amin, M.B., Hamid, S.H., and Rahman, F.; (1995), Prediction of mechanical properties of weather-induced degraded plastics in Saudi Arabia. Journal of Applied Polymer Science, 56: 279-284.

Gerlcok; On the use of Fourier transform infared spectroscopy and ultraviolet spectroscopy to assess the weathering performance of isolated clearcoats from different chemical families_Polymer Degradation and Stability 62 (1998) 225-234.

Adamson "Chemical surface Characterization and depth profiling of automotive coating systems" Prog. Polym. Sci. 25 (2000) 1363-1409.

Extended Search Report for EP Application No. 09251357.1 dated Oct. 9, 2009.

Extended Search Report for EP Application No. 1150399.1 dated Apr. 20, 2011.

United States Patent and Trademark Office; Office Action issued Jul. 16, 2012 in U.S. Appl. No. 12/684,368.

Lemaire, J. et al; Prediction of Coating Lifetime Based on FTIR Microspectrophotometric Analysis of Chemical Evolutions; Apr. 15, 1999; American Chemical Society, 246-256.

US Patent and Trademark Office; Final Office Action for U.S. Appl. No. 12/164,026 dated Sept 28, 2010.

US Patent and Trademark Office; Non-Final Office Action for U.S. Appl. No. 12/164,026 dated Mar. 29, 2010.

US Patent and Trademark Office; Final Office Action for U.S. Appl. No. 12/164,025 dated Sep. 1, 2010.

US Patent and Trademark Office; Non-Final Office Action for U.S. Appl. No. 12/164,025 dated Mar. 25, 2010.

US Patent and Trademark Office; Non-Final Office Action for U.S. Appl. No. 12/164,023 dated Nov. 29, 2010.

US Patent and Trademark Office; Non-Final Office Action for U.S. Appl. No. 12/164,023 dated Apr. 1, 2010.

United States Patent and Trademark Office; Office Action issued Dec. 12, 2011 in U.S. Appl. No. 12/684,368.

US Patent and Trademark Office; Non-Final Office Action for U.S. Appl. No. 12/164,022 dated May 27, 2011.

* cited by examiner

THERMAL EFFECT MEASUREMENT WITH NEAR-INFRARED SPECTROSCOPY

CROSS REFERENCE TO RELATED APPLICATIONS

This application is related to co-pending U.S. patent application Ser. Nos. 12/164,026, and 12/164,023; and 12/164,022, and 12/164,025, all filed concurrently herewith on Jun. 28, 2008, each of which applications is incorporated by reference herein in its entirety.

FIELD OF THE INVENTION

The disclosure relates to methods for determining thermal effect in composite materials. More particularly, the disclosure relates to a method for accurately assessing thermal effect in a composite material or surfacing film using near-infrared spectroscopy.

BACKGROUND OF THE INVENTION

Resin-fiber composite materials are utilized in a variety of applications including the aerospace industry, for example. Structures which are constructed of resin-fiber composite materials may be exposed to heat, which may affect the composite materials in various ways. These heat-induced effects may include chemical degradation in which changes such as oxidation, material loss and the breaking and/or forming of chemical bonds occurs in the polymer chemical structure of the composite materials. Resin decomposition, charring and fiber decomposition of the composite materials may occur at increasing temperatures.

Composite materials and epoxy-based surfacing films are typically cured under a vacuum at 250-350° F. for several hours. Repairs to the composite materials or surfacing films can become necessary if voids are found during an NDI inspection or if a flaw is found. These repairs may require the use of heating blankets that are notorious for having hot spots. Thus, during the repair some areas of the composite material or surfacing film may become overheated; in the case of epoxy-based surfacing films, a color change (dark or blackened) may be noticeable. Thermal effect may affect the mechanical and structural integrity of composite materials and surfacing films.

Repair or removal of heat-affected composite materials or surfacing films on a structure may involve first determining the degree of harmful thermal effect to the composite materials or surfacing films. Although determining the degree of thermal effect to composite materials or surfacing films may be performed by visual inspection, thermal effect may not be visually apparent. Current methods of determining the presence and extent of thermal effect in composite materials and surfacing films includes obtaining an infrared spectrum of a heat-affected composite standard and correlating the infrared spectrum obtained from the composite standard with the degree of thermal effect of the composite standard. An infrared spectrum obtained from the composite material or surfacing film the thermal effect of which is in question can then be compared to the infrared spectrum obtained from the composite standard to determine the presence and assess the degree of thermal effect in the composite material or surfacing film.

Calibration of infrared sensors to residual strength in composite materials or surfacing films correlates the resin condition as read from the infrared spectrum to the residual strength of the material or film which degrades as the resin degrades with progressively increasing temperatures. Therefore, the infrared sensors may be calibrated using time-controlled thermal soak standards which are obtained by exposing various composite materials or surfacing film controls to various temperatures for a particular time period such as one hour, for example. One method of preparing the standards includes placing the standards in an oven which is calibrated periodically and monitored continuously.

Near infrared radiation is capable of penetrating paint layers on a composite material or surfacing film to detect underlying composite material or film conditions. Hand-held near IR devices are generally less expensive than hand-held FT-IR devices and are often lighter and easier to use as well. Therefore, a method for accurately assessing thermal effect in a composite material or surfacing film using near-infrared spectroscopy is needed.

SUMMARY OF THE INVENTION

The disclosure is further generally directed to a method of determining a physical property of a composite material. An illustrative embodiment of the method includes providing a series of composite material standards with increasing thermal exposure (with or without a surfacing film), irradiating the composite material standards and/or the surfacing films with near-IR infrared energy, detecting near-infrared energy reflected from the composite material standards surfacing films, performing multivariate calibration on the series of the near-infrared spectra reflected from the composite material standards surfacing films, performing a multivariate calibration to the near-infrared spectra from the standards to make a model of the spectral changes with increasing thermal exposure (or decreasing mechanical properties), and using the multivariate model to predict the thermal exposure or mechanical properties of composite materials in question.

BRIEF DESCRIPTION OF THE ILLUSTRATIONS

DETAILED DESCRIPTION OF THE PREFERRED EMBODIMENT

Figure 1:
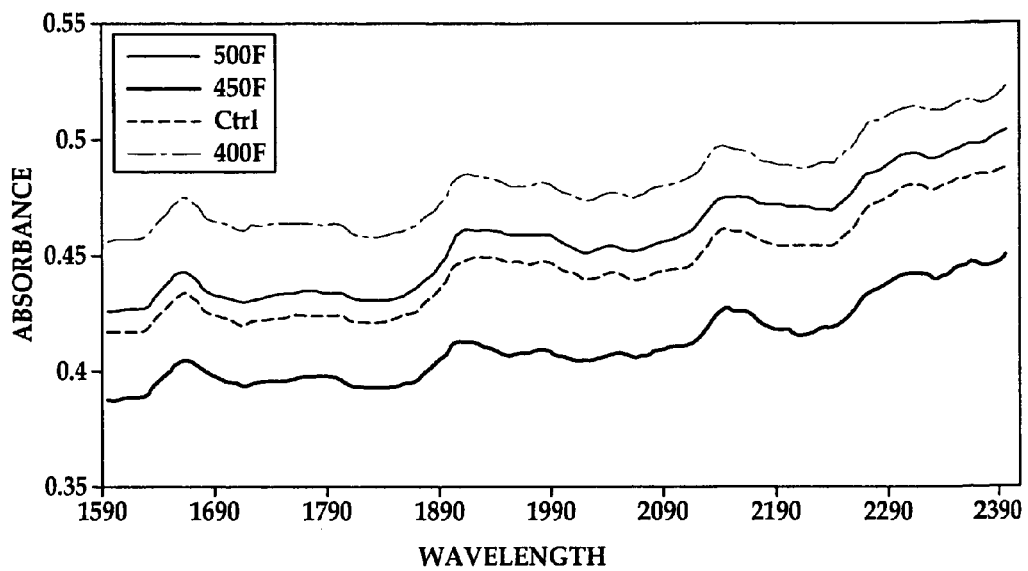
FIG. 1 is a series of near-IR spectra on thermally exposed graphite composite (CFRP) standards. These standards were exposed for 1 hour each at 400, 450, 500° F. and there is also one with no thermal exposure.
Figure 2:
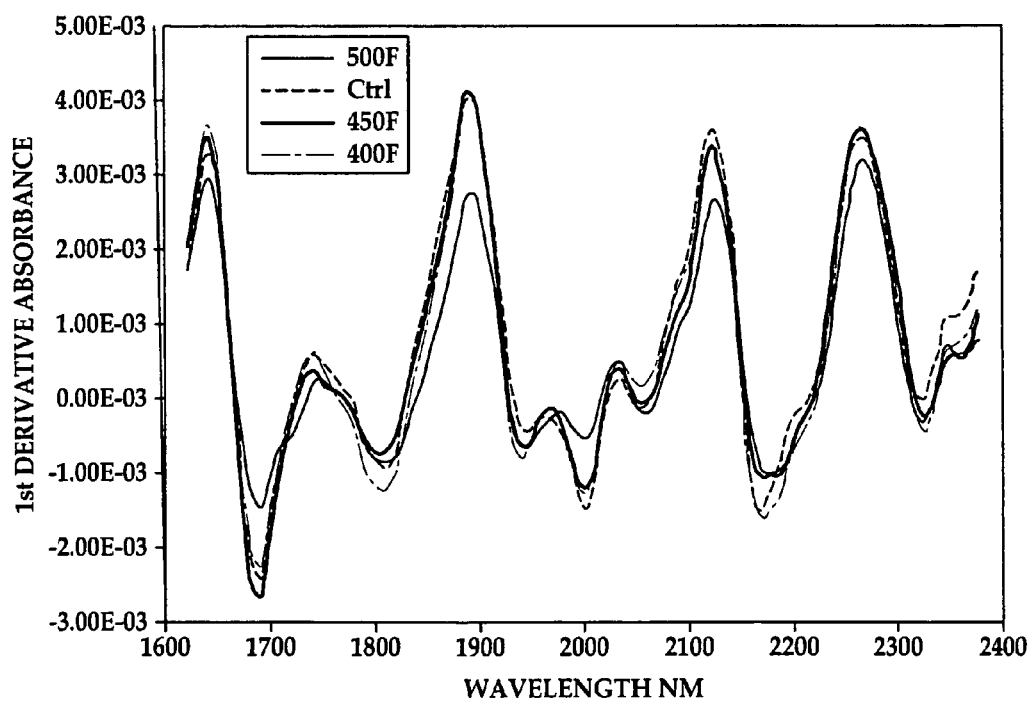
FIG. 2 is the same series of near-IR spectra from FIG. 1 but with first derivative and 7 point smoothing pre-processing with the Savitzky Golay method.
Figure 3:
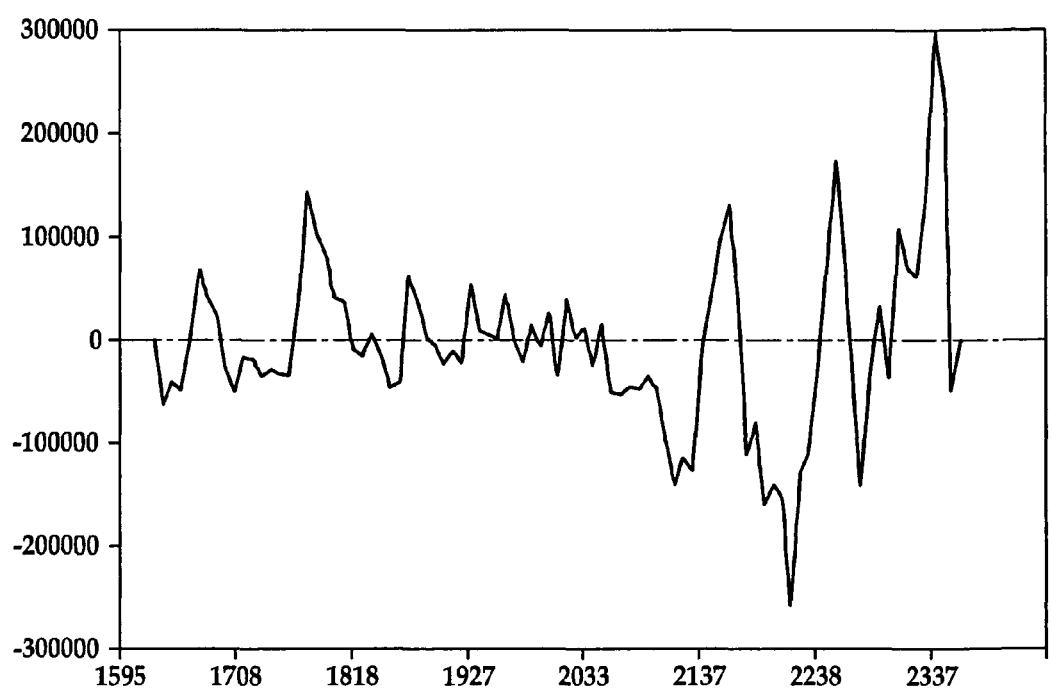
FIG. 3 is the regression vector from the multivariate calibration of the near-IR spectra to the un-notched compression test stress results of the standards using the PLS (partial least squares) multivariate calibration method.

Referring initially to FIGS. 1-4, an illustrative embodiment of a method of multivariate calibration for thermal effect with near-IR spectra is shown. As shown in block 402 of flow diagram 400 in FIG. 4, the thermal effect calibration begins with CFRP standards that are carefully cooked and then tested to obtain residual mechanical properties. Block 404 shows the mid-IR spectral data collection step and the raw infrared spectra are shown in FIG. 1. Block 406 shows the data preprocessing step and FIG. 2 shows the results of a typical pre-processing method. Block 408 shows the multivariate calibration step and FIG. 3 shows the regression coefficients that result from that calibration. Block 410 shows the step where the multivariate calibration is saved in an appropriate format and then loaded into the hand-held near-IR device that will be used to read thermal effect on CFRP material in question. Block 412 shows material in question being predicted for residual stress values that would indicate the extent of thermal effect in the material in question. If the original standards are predicted here, one can develop an accuracy figure for the methods based on the difference between the known stress numbers and those predicted by the method just developed.

Figure 4:
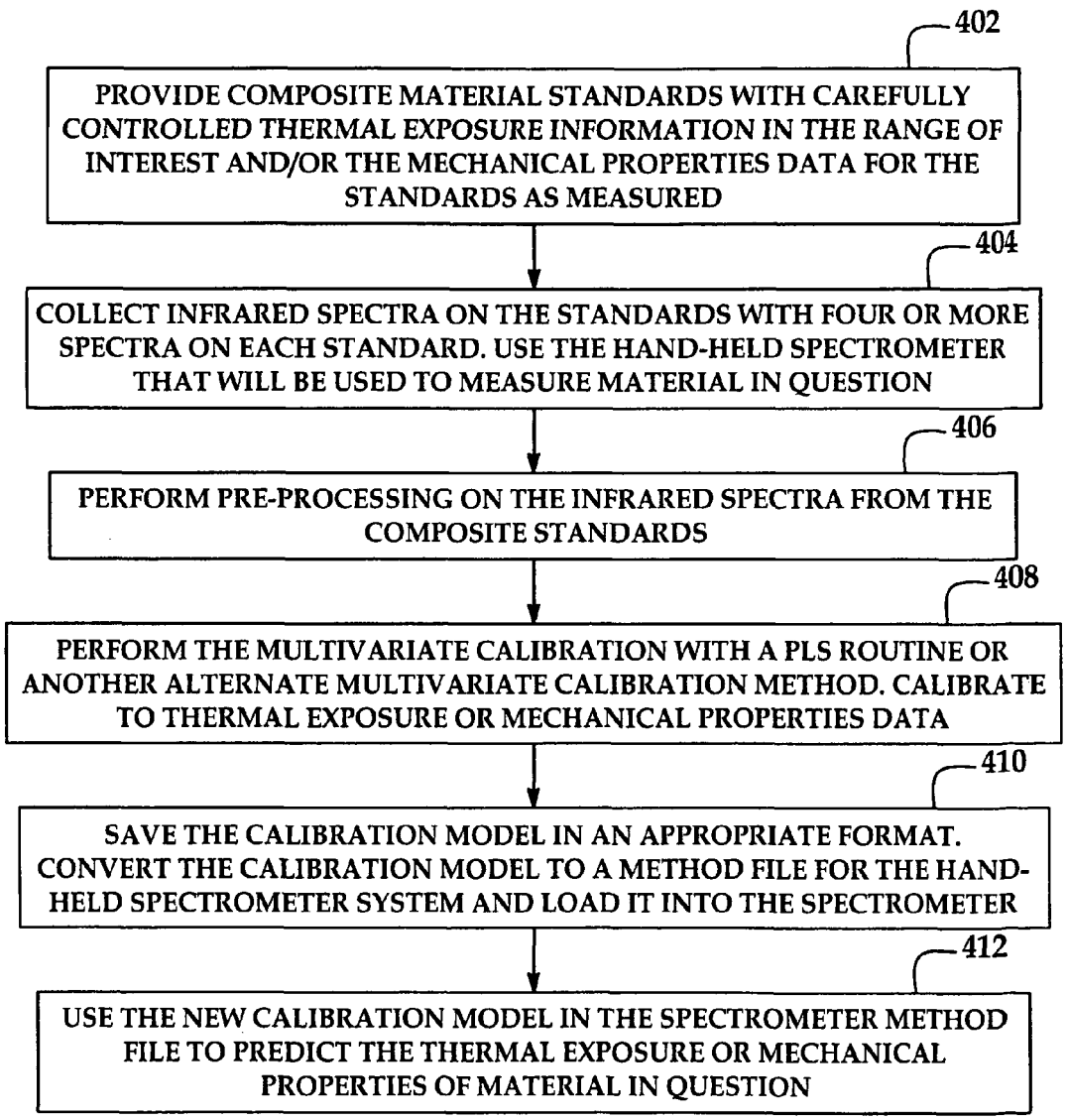
FIG. 4 is a flow diagram which illustrates the multivariate calibration and prediction method.
Figure 4A:
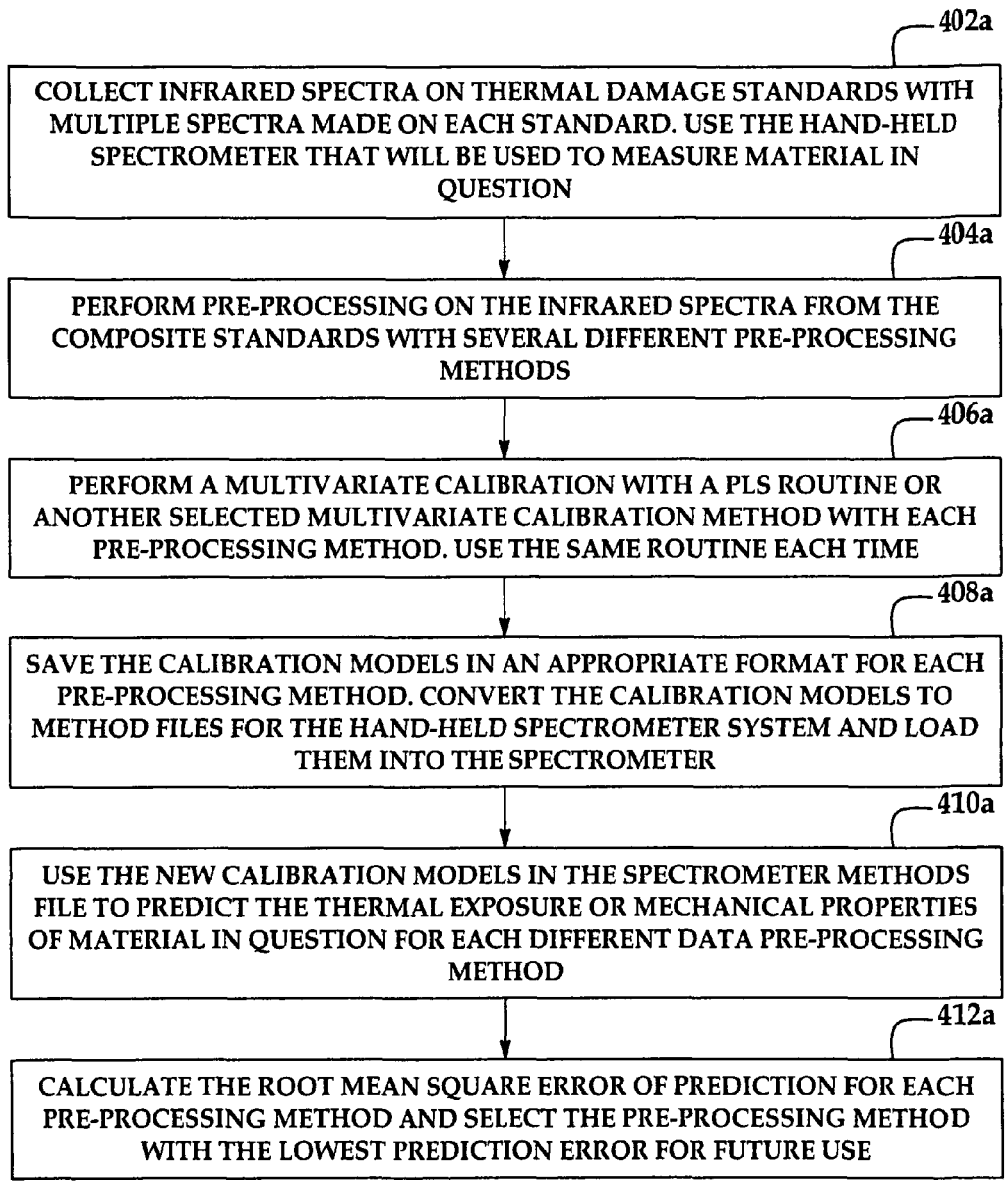
FIG. 4A is a flow diagram which illustrates important details in the multivariate calibration and prediction method.

Referring next to FIG. 4A, a flow diagram 400a which illustrates an illustrative embodiment of a method of optimizing the data pre-processing method for CFRP thermal effect calibration with multivariate methods. In block 402a, a thermal effect standard is provided. The thermal effect standard may have been fabricated according to the method which was heretofore described in a co-pending patent application assigned to the common assignee of the present disclosure filed as U.S. patent application Ser. No. 12/164,023, referenced above. In block 404a, the infrared spectra of the thermal effect standards are made using the near-IR wavelength range of from about 1.6 µm to about 2.4 µm. In block 404a, a surface of the thermal effect standard is irradiated with near-infrared energy having a wavelength of from about 0.75 µm to about 1.4 µm.

Figure 5:
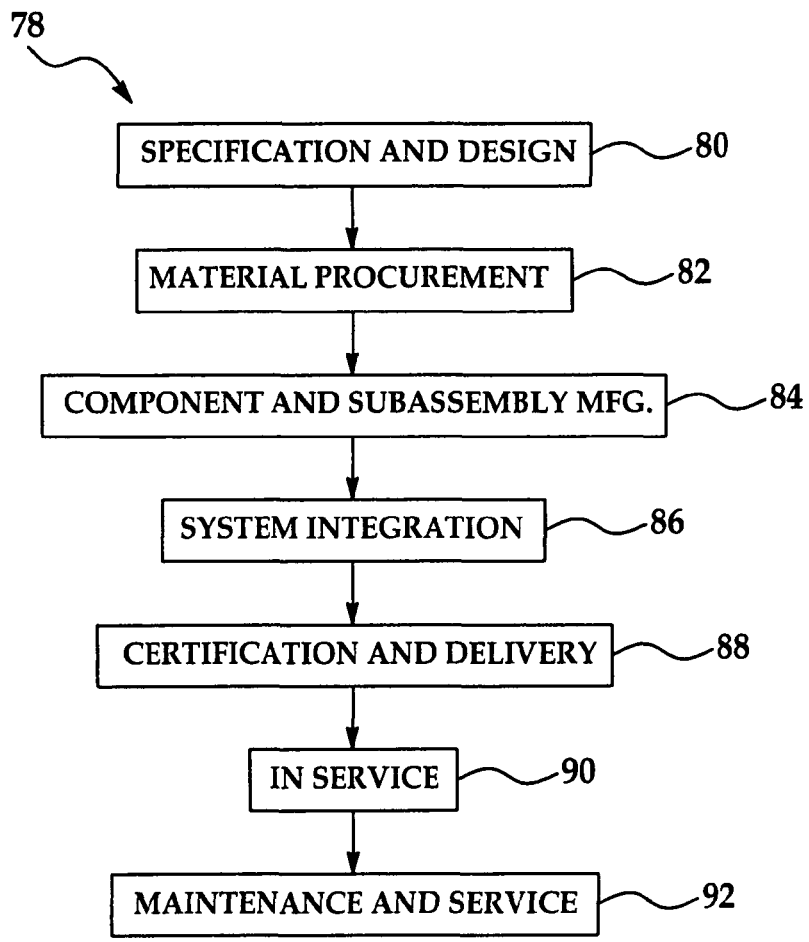
FIG. 5 is a flow diagram of an aircraft production and service methodology.
Figure 6:
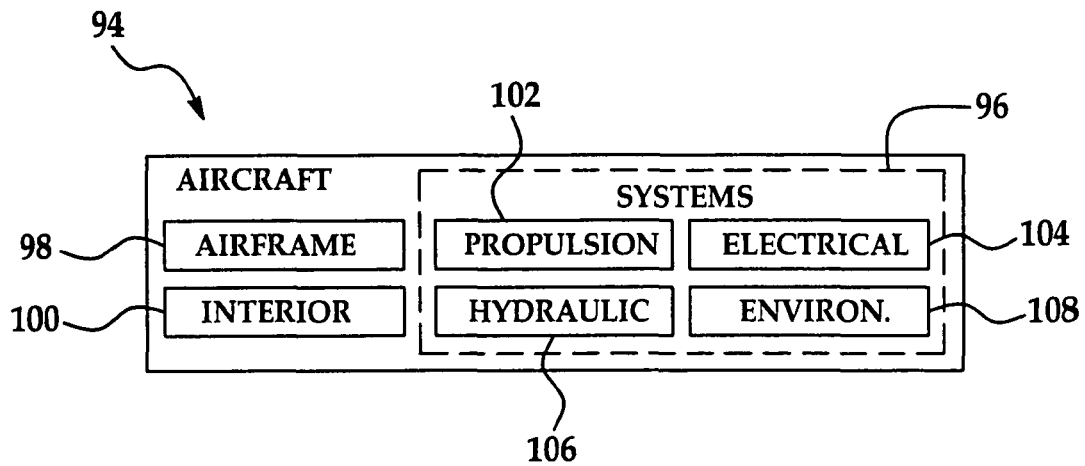
FIG. 6 is a block diagram of an aircraft.

Referring next to FIGS. 5 and 6, embodiments of the disclosure may be used in the context of an aircraft manufacturing and service method 78 as shown in FIG. 5 and an aircraft 94 as shown in FIG. 6. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 6, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also, one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A method of determining a physical property of a composite material, comprising:
   providing at least one of a composite material and a surfacing film standard;
   irradiating said standard with near-infrared energy;
   detecting near-infrared energy reflected from said standard;
   performing pre-processing on infrared spectra from said standard with a plurality of pre-processing methods;
   performing multivariate analysis on a spectrum of said near-infrared energy reflected from said standard;
   subjecting said standard to mechanical tests to obtain a residual strength of said standard;
   obtaining a correlation of a spectrum of near-infrared energy reflected from said standard;
   quantifying a degree of thermal effect to said standard by comparing results of said multivariate analysis with said correlation;
   predicting thermal exposure or mechanical properties of a material in question based on said degree of thermal effect;
   calculating root mean square error of prediction for each of said plurality of pre-processing methods; and
   selecting from said plurality of pre-processing methods a pre-processing method having a lowest prediction error for future use.

2. The method of claim 1 wherein said at least one of a composite material and a surfacing film comprises a resin-fiber composite material.

3. The method of claim 1 wherein said at least one of a composite material and a surfacing film comprises an epoxy-based surfacing film.

4. The method of claim 1 wherein said providing at least one thermal effect standard comprises providing at least one of a composite material specimen and a surfacing film specimen and heating said at least one of a composite material specimen and- a surfacing film specimen.

5. The method of claim 1 wherein said providing a thermal effect standard comprises providing a specimen oven, precisely calibrating said specimen oven to at least one exposure temperature, placing at least one of a composite material specimen and a surfacing film specimen in said specimen oven and operating said specimen oven at said at least one exposure temperature.

6. The method of claim 5 wherein said precisely calibrating said specimen oven to at least one exposure temperature comprises providing at least one thermocouple, placing said at least one thermocouple in said specimen oven and operating said specimen oven at said exposure temperature as indicated by said at least one thermocouple.

7. The method of claim 1 wherein said providing at least: one thermal effect standard comprises providing a plurality of thermal effect standards having various degrees of heat effect.

8. A method of determining a physical property of a composite material, comprising:
providing at least one of a composite material and a surfacing film standard;
irradiating said standard with near-infrared energy having a wavelength of from about 0.75 um to about 1.4 um;
detecting near-infrared energy reflected from said standard;
performing pre-processing on infrared spectra from said standard with a plurality of pre-processing methods;
performing multivariate analysis on a spectrum of said near-infrared energy reflected from said standard;
subjecting said standard to mechanical tests to obtain a residual strength of said standard;
obtaining a correlation of a spectrum of near-infrared energy reflected from said standard;
quantifying a degree of heat effect to said standard by comparing results of said multivariate analysis with said correlation;
predicting thermal exposure or mechanical properties of a material in question based on said degree of heat effect;
calculating root mean square error of prediction for each of said plurality of pre-processing methods; and
selecting from said plurality of pre-processing methods a pre-processing method having a lowest prediction error for future use.

9. The method of claim 8 wherein said at least one of a composite material and a surfacing film comprises a resin-fiber composite material.

10. The method of claim 8 wherein said at least one of a composite material and a surfacing film comprises an epoxy-based surfacing film.

11. The method of claim 8 wherein said providing at least one thermal effect standard comprises providing at least one of a composite material specimen and a surfacing film specimen and heating said at least one of a composite material specimen and a surfacing film specimen.

12. The method of claim 8 wherein said providing a thermal effect standard comprises providing a specimen oven, precisely calibrating said specimen oven to at least one exposure temperature, placing at least one of a composite material specimen and a surfacing film specimen in said specimen oven and operating said specimen oven at said at least one exposure temperature.

13. The method of claim 12 wherein said precisely calibrating said specimen oven to at least one exposure temperature comprises providing at least one thermocouple, placing said at least one thermocouple in said specimen oven and operating said specimen oven at said exposure temperature as indicated by said at least one thermocouple.

14. The method of claim 8 wherein said providing at least one thermal effect standard comprises providing a plurality of thermal effect standards having various degrees of heat effect.

15. A method of determining a physical property of a composite material, comprising:
providing at least one of a composite material and a surfacing film standard;
irradiating said at least one of a composite material and a surfacing film standard with near-infrared energy;
detecting near-infrared energy reflected from said at least one of a composite material and a surfacing film standard;
performing pre-processing on infrared spectra from said standard with a plurality of pre-processing methods;
performing multivariate analysis on a spectrum of said near-infrared energy reflected from said at least one of a composite material and a surfacing film standard;
providing at least one thermal effect standard by:
providing an oven;
placing at least one thermocouple at a measurement location in said oven;
operating said oven;
monitoring a temperature output of said at least one thermocouple;
providing at least one of a composite material specimen and a surfacing film specimen;
placing said at least one of a composite material specimen' and a surfacing film specimen at said measurement location in said oven;
heat treating said at least one of composite material specimen and a surfacing film specimen as at least one thermal effect standard by operating said oven according to said temperature output of said at least one thermocouple; and
subjecting said at least one thermal effect standard to mechanical tests to obtain a residual strength of said at least one thermal effect standard;
obtaining a correlation of a spectrum of near-infrared energy reflected from said at least one thermal effect standard and said residual strength of said at least one thermal effect standard;
quantifying a degree of heat effect to said at least one of a composite material and a surfacing film by comparing results of said multivariate analysis with said correlation;
predicting thermal exposure or mechanical properties of a material in question based on said degree of heat effect;
calculating root mean square error of prediction for each of said plurality of pre-processing methods; and
selecting from said plurality of pre-processing methods a pre-processing method having a lowest prediction error for future use.

16. The method of claim 15 wherein said irradiating said at least one of a composite material and a surfacing film with near-infrared energy comprises irradiating said at least one of a composite material and a surfacing film with near-infrared energy having a wavelength of from about 0.75 um to about 1.4 um.

17. The method of claim 15 further comprising placing metal plates at said measurement location in said oven and wherein said placing at least one thermocouple at a measurement location in said oven comprises placing a bundle of thermocouples between said metal plates.

* * * * *